(12) United States Patent
Aleksov et al.

(10) Patent No.: US 8,324,274 B2
(45) Date of Patent: Dec. 4, 2012

(54) DRUG DELIVERY SYSTEM FOR ADMINISTRATION OF A WATER SOLUBLE, CATIONIC AND AMPHIPHILIC PHARMACEUTICALLY ACTIVE SUBSTANCE

(75) Inventors: Julian Aleksov, Lidingö (SE); Igor Lokot, Uppsala (SE)

(73) Assignee: Ardenia Invesments, Ltd., London, Greater London (GB)

( * ) Notice: Subject to any disclaimer, the term of this patent is extended or adjusted under 35 U.S.C. 154(b) by 78 days.

(21) Appl. No.: 12/809,265

(22) PCT Filed: Dec. 18, 2008

(86) PCT No.: PCT/SE2008/051517
§ 371 (c)(1),
(2), (4) Date: Sep. 15, 2010

(87) PCT Pub. No.: WO2009/078804
PCT Pub. Date: Jun. 25, 2009

(65) Prior Publication Data
US 2011/0236472 A1    Sep. 29, 2011

(30) Foreign Application Priority Data

Dec. 19, 2007  (WO) ................ PCT/SE2007/001128

(51) Int. Cl.
| A61K 37/00 | (2006.01) |
| A61K 31/22 | (2006.01) |
| C07C 309/00 | (2006.01) |
| C07C 313/00 | (2006.01) |

(52) U.S. Cl. ......... 514/553; 514/550; 562/106; 562/126
(58) Field of Classification Search ......................... None
See application file for complete search history.

(56) References Cited

U.S. PATENT DOCUMENTS

| 6,197,809 B1 | 3/2001 | Strelchenok |
| 2004/0048923 A1 | 3/2004 | Strelchenok et al. |
| 2005/0191359 A1 | 9/2005 | Goldshtein et al. |
| 2007/0082838 A1 | 4/2007 | De et al. |

FOREIGN PATENT DOCUMENTS

| EP | 1 666 031 A1 | 6/2006 |
| WO | 01/17546 | 3/2001 |
| WO | 02/092600 | 11/2002 |
| WO | 2005/089106 | 9/2005 |
| WO | 2006/106519 | 10/2006 |
| WO | 2007/001356 | 1/2007 |
| WO | 2009/078802 | 6/2009 |
| WO | 2009/078803 | 6/2009 |

OTHER PUBLICATIONS

Torchilin, V.P.; Pharmaceutical Research, vol. 24, No. 1, Jan. 2007, pp. 1-16.*
Saadia Hassan et al., "Cytotoxic activity of a new paclitaxel formulation, Pacliex, in vitro and in vivo", Cancer Chemother Pharmacol, 2005, vol. 55, pp. 47-54.
D. V. Arsenov et al., "Synthesis of N-(all-transretinoyl)doxorubicin and study of the antitumor activity of its complex with blood serum proteins", Pharmaceutical Chemistry Journal, 2001, vol. 35, No. 4, pp. 186-189.
Mahesh Chavanpatil et al., "Polymer-Surfactant Nanoparticles for Sustained Release of Water-Soluble Drugs", Journal of Pharmaceutical Sciences, Dec. 2007, vol. 96, No. 12 pp. 3379-3389.
International Search Report for corresponding International Application No. PCT/SE2008/051516 mailed Mar. 20, 2009.
Written Opinion for corresponding International Application No. PCT/SE2008/051516 mailed Mar. 20, 2009.
Written Opinion of the International Preliminary Examining Authority for corresponding International Application No. PCT/SE2008/051516 mailed Nov. 20, 2009.
International Preliminary Report on Patentability for corresponding International Application No. PCT/SE2008/051516 mailed Mar. 25, 2010.
International Search Report for corresponding International Application No. PCT/SE2008/051515 mailed Mar. 20, 2009.
Written Opinion for corresponding International Application No. PCT/SE2008/051515 mailed Mar. 20, 2009.
Written Opinion of the International Preliminary Examining Authority for corresponding International Application No. PCT/SE2008/051515 mailed Nov. 20, 2009.
International Preliminary Report on Patentability for corresponding International Application No. PCT/SE2008/051515 mailed Oct. 19, 2009.
International Search Report for corresponding International Application No. PCT/SE2008/051517 mailed Mar. 20, 2009.
Written Opinion for corresponding International Application No. PCT/SE2008/051517 mailed Mar. 20, 2009.
PCT Communication in Cases for Which No Other Form is Suitable—Corrected International Search Report and Written Opinion for corresponding International Application No. PCT/SE2008/051517 mailed Apr. 1, 2009.
Written Opinion of the International Preliminary Examining Authority for corresponding International Application No. PCT/SE2008/051517 mailed Nov. 20, 2009.
International Preliminary Report on Patentability for corresponding International Application No. PCT/SE2008/051517 mailed Mar. 25, 2010.

* cited by examiner

*Primary Examiner* — Robert A Wax
*Assistant Examiner* — Jeffrey T Palenik
(74) *Attorney, Agent, or Firm* — Renner, Otto, Boisselle & Sklar, LLP

(57) ABSTRACT

A drug delivery system (DDS) for administration of a water soluble, cationic, and amphiphilic pharmaceutically active substance (API) which DDS comprises amorphous particles of <100 nm of a poorly water soluble complex of the API with a Na-salt of N-all-trans-retinoyl cysteic acid methyl ester and/or a Na-salt of N-13-cis-retinoyl cysteic acid methyl ester, which particles are entrapped in nanoparticles formed a Na-salt of N-all-trans-retinoyl cysteic acid methyl ester and/or a Na-salt of N-13-cis-retinoyl cysteic acid methyl ester, the w/w-ratio of Na-salt of N-alltrans-retinoyl cysteic acid methyl ester and/or a Na-salt of N-13-cis-retinoyl cysteic acid methyl ester to the complex is about 0.5:1 to about 20:1. A pharmaceutical composition comprising such a DDS. Methods for preparation of such a DDS and such a pharmaceutical composition. Use of such a DDS and pharmaceutical composition for treatment of cancer.

30 Claims, 2 Drawing Sheets

DRUG DELIVERY SYSTEM FOR ADMINISTRATION OF A WATER SOLUBLE, CATIONIC AND AMPHIPHILIC PHARMACEUTICALLY ACTIVE SUBSTANCE

This application is a national phase of International Application No. PCT/SE2008/051517 filed Dec. 18, 2008 and published in the English language, which claims priority to International Application No. PCT/SE2007/001128 filed Dec. 19, 2007.

FIELD OF THE INVENTION

This invention relates to a drug delivery system for administration of pharmaceutically active substances, a pharmaceutical composition comprising such a drug delivery system, and methods for the preparation of such a drug delivery system. Furthermore the invention also relates to the use of such a drug delivery system for the preparation of a medicament for the treatment of cancer.

BACKGROUND OF THE INVENTION

Drugs with narrow therapeutic indexes carry the disadvantage that small changes in the dosage can cause toxic effects. Patients taking such drugs often require extensive monitoring so that the level of medication can be adjusted to assure uniform and safe results. There is an imperative demand for doing away with the need for such monitoring without jeopardizing uniform and safe results. This need becomes particularly pronounced when such drugs are used in combination therapy.

Combination therapy, that is simultaneous administration of two or more medications to treat a single disease, is used in the treatment of a great number of conditions, such as for instance tuberculosis, leprosy, cancer, malaria, and HIV/AIDS.

In many instances, combination therapy carries a number of advantages, such as lower treatment failure rate, lower case-fatality ratios, slower development of resistance—and also less need for development of new drugs. However, combination therapy also suffers from a number of potential disadvantages, such as antagonism between the combined drugs, leading to reduction of their individual activity; increased risk of detrimental drug-drug interactions; increased cost compared with monotherapy; and increase in the potential for drug-related toxicity.

Combination chemotherapy is used extensively in the treatment of different types of cancer as it improves the survival profile compared to monotherapy. A better outcome can be obtained by combining antineoplastic agents with different mechanism of action that provides synergistic or additive effects during therapy.

The main problem with combination chemotherapy is the increase of toxicity compared with sequential administration of single agents. This may not be counterbalanced by limiting the doses, as this would lead to doses below the therapeutic ones. Different agents also have different pharmacokinetic properties and this makes it difficult to maintain the concentrations of all of them at optimal synergistic levels in the target tissues.

Doxorubicin is a drug commonly used in combination chemotherapy. It has an excellent antitumor activity, but unfortunately also a relatively low therapeutic index, as well as a broad spectrum of side effects which limits the use of it. One such side effect is cardiotoxicity, which is usually developed as an acute or subacute syndrome. At greater drug exposure myocardial damage may occur, and it is recommended that the cumulative lifetime dose of doxorubicin does not exceed 450-550 mg/m$^2$. This cardiotoxicity is the main cause for preventing doxorubicin to be used in elderly patients and in patients with pre-existing cardiac disease.

Several attempts have been made to provide anthracyclines/taxanes combinations, for instance of doxorubicin and docetaxel, using conventional formulations. These compounds demonstrate high monotherapy activity with different mechanisms of action: doxorubicin inhibits the progression of the enzyme topoisimerase II throughout the whole cell cycle while docetaxel hinders a mitotic cell division between metaphase and anaphase by preventing physiological microtubule depolymerisation/disassembly. The provided combinations have shown to be more effective than the corresponding monotherapies, but also involving higher toxicity. This precludes the therapy from becoming a standard method for treatment of different types of cancer, especially in case of certain conditions such as febrile neutropenia.

DESCRIPTION OF THE INVENTION

It would be desirable to be able to create a drug delivery system that would diminish the need for extensive monitoring of patients taking drugs with narrow therapeutic indexes.

One object of the present invention is to provide such a drug delivery system.

Another object of the present invention is to provide a drug delivery system that would reduce or eliminate drug-related toxicity associated with combination therapy.

Thus, one embodiment of the invention relates to a drug delivery system for administration of at least one pharmaceutically active substance that is a cationic amphiphile by itself, which pharmaceutically active substance is present in the drug delivery system in particles of a complex between said pharmaceutically active substance and a sodium salt of the methyl ester of N-all-trans-retinoyl cysteic acid, a sodium salt of methyl ester of N-13-cis-retinoyl cysteic acid, or a combination thereof, said particles of said complex having an effective average particle size of less than about 100 nm, wherein
  the particles of said complex are essentially amorphous;
  the particles of said complex are entrapped in nanoparticles formed of a sodium salt of the methyl ester of N-all-trans-retinoyl cysteic acid, sodium salt or methyl ester of N-13-cis-retinoyl cysteic acid, or a combination thereof; and
  the weight-to-weight ratio of said sodium salt or methyl ester of N-all-trans-retinoyl cysteic acid, sodium salt or methyl ester of N-13-cis-retinoyl cysteic acid, or combination thereof, to the weight of said complex is in the range from about 0.5:1 to about 20:1.

The therapeutic indexes of various pharmaceuticals are significantly improved by the present drug delivery system. Side-effects mainly caused by high concentrations of drugs directly after infusions are significantly reduced by the use of the present drug delivery system, as it mimics prolonged infusion. The encapsulated substances are prevented from being metabolised, and they are released gradually by dissolvation/erosion of the particles, which helps to maintain the drug concentration within the therapeutic window. It should be noted that apart from toxic concentrations also sub-therapeutic concentrations, which could otherwise lead to development of drug resistance, are avoided by the present invention.

The encapsulation of different types of pharmaceuticals into nanoparticles obtained by the present drug delivery system provides simultaneous transfer of these substances to the targets of action, synchronizing their otherwise different pharmacokinetic profiles (the half life of docetaxel is for instance five times higher than for doxorubicin), thus stimulating development of a synergistic action of the constituents of the combination.

The present invention is applicable for the creation of combination formulations of two or more kinds of pharmaceutically active substances, such as for instance antineoplastic substances.

Among drugs which can be used in the present drug delivery systems are water soluble antineoplastic agents, for instance such agents containing one or more amino groups, e.g. anthracycline hydrochlorides. According to one aspect of the present invention the solubility of such anthracycline salts is significantly reduced by replacing the chloride anion with an anion of the methyl ester of N-all-trans-retinoyl cysteic acid, methyl ester of N-13-cis-retinoyl cysteic acid, or a combination thereof. The resulting insoluble complexes allow theses anthracycline derivative to be loaded in nanoparticle of the present drug delivery system, ensuring slow release of the drugs. Exemplary of such anthracyclines are doxorubicin, daunorubicin, epirubicin, idarubicin, mitoxantrone and natural, synthetic and semi-synthetic analogous thereof.

Among other kinds of substances that can be used in combinations provided by the present invention are:

Water insoluble antineoplastic agents, such as taxanes, for instance paclitaxel, docetaxel and natural, synthetic and semi-synthetic analogous thereof;

Vinca alkaloids, such as for instance vincristine, vinblastine, vinorelbine, vindesine and natural, synthetic and semi-synthetic analogous thereof;

Topoisomerase inhibitors, such as for instance irinotecan, topotecan, etoposide, teniposide and natural, synthetic and semi-synthetic analogous thereof; and Alkylating agents, such as for instance amsacrine, procarbazine, bischloronitrosourea and analogous thereof.

The inventive combination formulations can be provided in various aqueous solutions. They can be directly administered or freeze dried for future use.

The size of the particles in the obtained inventive drug delivery systems lies in the range of about 8-100 nm.

Cryogenic transmission electron microscopy shows that inventive drug delivery systems comprising taxanes and doxorubicin consist of threadlike particles with a size of about 20 nm, which are sometimes entangled into bigger aggregates. Dilution of the formulations results in a reduction of size of aggregates.

BRIEF DESCRIPTION OF THE DRAWINGS

The present invention will be described in closer detail in the following description, examples and attached drawings, in which.

DESCRIPTION OF EMBODIMENTS OF THE INVENTION

Figure 1:
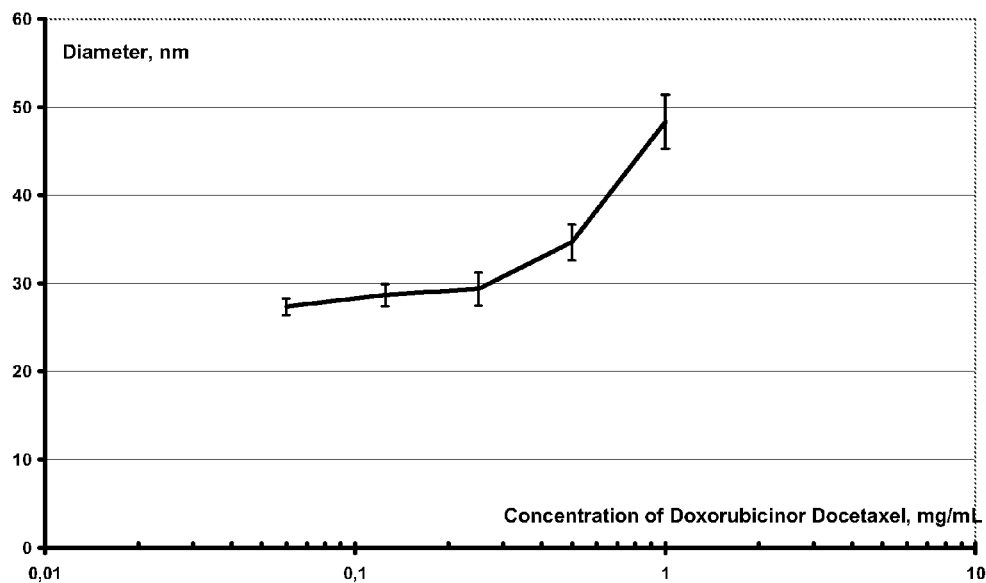
FIG. 1 shows the size of the particles formed by doxorubicin, docetaxel, sodium salt of methyl ester of N-all-trans-retinoyl cysteic acid and sodium salt of methyl ester of N-13-cis-retinoyl cysteic acid (w/w/w 1:1:1.65:1.65) at different dilutions. Solvent: aqueous solution of NaCl (5.9 mg/mL), KCl (0.3 mg/mL), CaCl$_2$ (0.295 mg/mL), MgCl$_2$ hexahydrate (0.2 mg/mL), sodium acetate (4.1 mg/mL).
Figure 2:
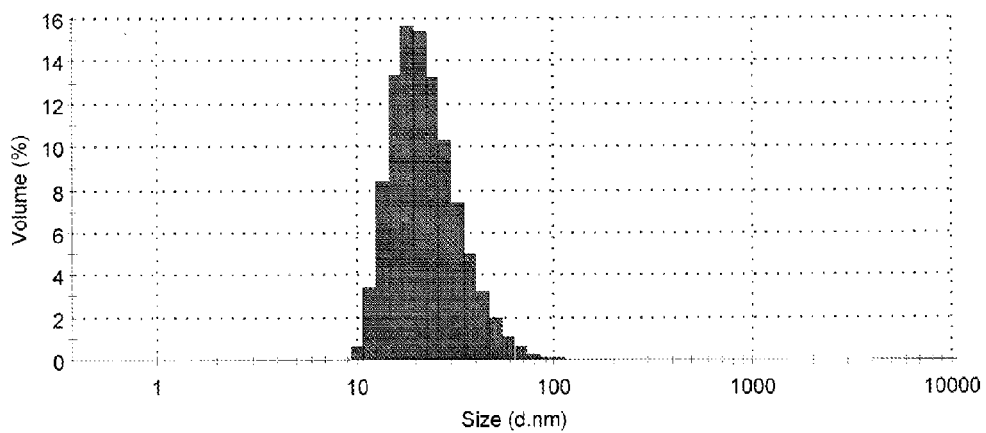
FIG. 2 shows the particle size distribution by volume of formulation obtained by reconstitution of freeze-dried mixture of doxorubicin, docetaxel, sodium salt of methyl ester of N-all-trans-retinoyl cysteic acid and sodium salt of methyl ester of N-13-cis-retinoyl cysteic acid (w/w/w 1:1:1.65:1.65). Solvent: aqueous solution of NaCl (5.9 mg/mL), KCl (0.3 mg/mL), CaCl$_2$ (0.295 mg/mL), MgCl$_2$ hexahydrate (0.2 mg/mL), sodium acetate (4.1 mg/mL). Doxorubicin concentration 0.5 mg/mL.
Figure 3:
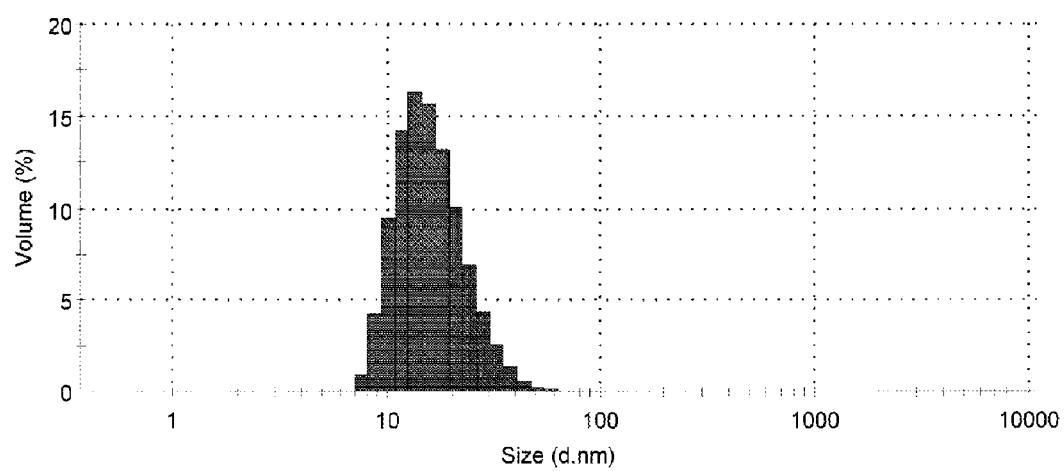
FIG. 3 shows the particle size distribution by volume of formulation obtained by reconstitution of freeze-dried mixture of doxorubicin, paclitaxel, sodium salt of methyl ester of N-all-trans-retinoyl cysteic acid and sodium salt of methyl ester of N-13-cis-retinoyl cysteic acid (w/w/w 1:2.5:3:3). Solvent: aqueous solution of NaCl (5.9 mg/mL), KCl (0.3 mg/mL), CaCl$_2$ (0.295 mg/mL), MgCl$_2$ hexahydrate (0.2 mg/mL), sodium acetate (4.1 mg/mL). Paclitaxel concentration 1 mg/mL.

Before the present invention is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the claims, the singular forms "a", "an", and "the" include plural referents unless the context clearly dictates otherwise.

In this specification, unless otherwise stated, the term "about" modifying the quantity of an ingredient in the drug delivery systems or compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the drug delivery systems or compositions or carry out the methods; and the like. The term "about" also encompasses amounts that differ due to different equilibrium conditions for a composition resulting from a particular initial mixture. Whether or not modified by the term "about", the claims include equivalents to the quantities.

In this specification, unless otherwise stated, the term "drug delivery system" refers to a formulation or device that delivers therapeutic agent(s) to desired body location(s) and/or provides timely release of therapeutic agent(s).

In this specification, unless otherwise stated, the term "particle size" refers to the Z-average diameter as measured by dynamic light scattering with the use of red laser with a wavelength of 633 nm. By "an effective average particle size of less than about 100 nm" it is meant that at least 90% of the particles have a size of less than about 100 nm when measured by the above-noted technique.

In this specification, unless otherwise stated, the term "nanoparticle" refers to a microscopic particle whose size is measured in nanometers. Nanoparticles of the invention typically range from about 1 to about 999 nm in diameter, and can include an entrapped, encapsulated, or enclosed biologically active molecule.

In this specification, unless otherwise stated, the term "solubility" of a substance refers to the ability of that substance to be dissolved in a specified solvent at about room temperature, by which is meant from between about 15° C. to about 38° C.

In this specification, unless otherwise stated, the term "amorphous" is intended to indicate a solid structure that is either non-crystalline or consists of very small crystals having a particle size of about 10 nm or less.

In this specification, unless otherwise stated, the term "cytotoxic compound" refers to a compound that has the ability of arresting the growth of, or killing, cells.

In this specification, unless otherwise stated, the term "cytostatic compound" refers to a compound that has the ability of bringing cells, although not necessarily lysed or killed, into a permanent non-proliferative state.

In this specification, unless otherwise stated, the term "derivative" refers to a compound formed from the original structure either directly, by chemical reaction of the original structure, or by a "modification" which is a partial substitution of the original structure, or by design and de novo synthesis. Derivatives may be synthetic, or may be metabolic products of a cell or an in vitro enzymatic reaction.

In one embodiment of the inventive drug delivery system the pharmaceutically active substance has a solubility per se in water of at least 4 mg/ml, and that said complex is a non-covalent complex having a solubility in water of below 0.1 mg/ml.

In another embodiment of the inventive drug delivery system said complex has an effective average particle size of less than about 50 nm. Smaller particles are less likely to be detected by the reticulo-endothelial system which protects the body against invading microorganisms like viruses and bacteria.

In a further embodiment of the inventive drug delivery system the weight-to-weight ratio of said sodium salt of the methyl ester of N-all-trans-retinoyl cysteic acid, sodium salt of the methyl ester of N-13-cis-retinoyl cysteic acid, or combination thereof, to the weight of said complex is in the range from about 1:1 to about 10:1.

In another embodiment of the present invention the drug delivery system comprises at least one other pharmaceutically active substance having a solubility per se in water of less than about 100 μg/ml, said other pharmaceutically active substance being in particulate form with an effective average particle size of less than about 100 nm, wherein the particles of said other pharmaceutically active substance are essentially amorphous; the particles of said other pharmaceutically active substance are entrapped together with the particles of said complex in said nanoparticles; and the weight-to-weight ratio of said sodium salt or methyl ester of N-all-trans-retinoyl cysteic acid, sodium salt or methyl ester of N-13-cis-retinoyl cysteic acid, or combination thereof, to the combined weight of said other pharmaceutically active substance and said complex is in the range from about 0.5:1 to about 20:1. In one aspect of this embodiment said complex has an effective average particle size of less than about 50 nm. In another aspect of this embodiment the weight-to-weight ratio of said sodium salt of the methyl ester of N-all-trans-retinoyl cysteic acid, sodium salt of the methyl ester of N-13-cis-retinoyl cysteic acid, or combination thereof, to the weight of said complex is in the range from about 1:1 to about 10:1. According to a further aspect of this embodiment said other pharmaceutically active substance has an effective average particle size of less than about 50 nm, and/or said complex has an effective average particle size of less than about 50 nm. In a yet further aspect of this embodiment the weight-to-weight ratio of said sodium salt of the methyl ester of N-all-trans-retinoyl cysteic acid, sodium salt of the methyl ester of N-13-cis-retinoyl cysteic acid, or combination thereof, to the combined weight of said other pharmaceutically active substance and said complex is in the range from about 1:1 to about 10:1.

In another embodiment of the present invention at least one of said pharmaceutically active substances is a cytotoxic or a cytostatic compound.

In a further embodiment of the present invention said at least one pharmaceutically active substance is a cytotoxic or cytostatic compound. In one aspect of this embodiment said cytotoxic or cytostatic compound is a protonated form of doxorubicin, mitoxantrone, epirubicin, daunorubicin, idarubicin, topotecan, irinotecan, vinblastine, vincristine, vinorelbine, amsacrine, procarbazine, mechlorethamine, or a combination thereof. In a more specific aspect of this embodiment said compound is a protonated form of doxorubicin; in another more specific aspect of this embodiment said compound is a protonated form of mitoxantrone.

In another aspect of the embodiment of the present invention in which the drug delivery system comprises at least one other pharmaceutically active substance having a solubility per se in water of less than about 100 μg/ml said other pharmaceutically active substance is a cytotoxic or cytostatic compound. In a further aspect of this embodiment said cytotoxic or cytostatic compound is a taxane. In a yet further aspect of this embodiment said taxane is chosen among paclitaxel, docetaxel, and derivatives thereof. In another aspect of this embodiment said at least one pharmaceutically active substance and said other pharmaceutically active substance are cytotoxic or cytostatic compounds; in one aspect of this embodiment said at least one pharmaceutically active substance is a protonated form of doxorubicin, mitoxantrone, epirubicin, daunorubicin, idarubicin, topotecan, irinotecan, vinblastine, vincristine, vinorelbine, amsacrine, procarbazine, mechlorethamine, or a combination thereof; in a specific aspect of this embodiment said compound is a protonated form of doxorubicin; in further specific aspect of this embodiment said compound is a protonated form of mitoxantrone; in another specific aspect of this embodiment said other pharmaceutically active substance is a taxane; in a further specific aspect of this embodiment said taxane is chosen among paclitaxel, docetaxel, and derivatives thereof.

Another embodiment of the present invention relates to said drug delivery system of for use in treatment of cancer.

Another embodiment of the invention relates to a pharmaceutical composition comprising a pharmaceutically acceptable carrier and a drug delivery system of said kind. In one aspect of this embodiment the pharmaceutical composition is in the form of an aqueous solution, a gel, a cream, an ointment, a tablet, a capsule, or a softgel.

Another embodiment of the invention relates to the use of a sodium salt of the methyl ester of N-all-trans-retinoyl cysteic acid, a sodium salt of the methyl ester of N-13-cis-retinoyl cysteic acid, or a combination thereof, in the preparation of the drug delivery system according to the present invention.

Yet another embodiment the present invention relates to method for the preparation of a drug delivery system of the inventive kind in which the size of said complex is controlled to have an effective average particle size of less than about 100 nm by adjusting the weight-to-weight ratio of said sodium salt of the methyl ester of N-all-trans-retinoyl cysteic acid, sodium salt of the methyl ester of N-13-cis-retinoyl cysteic acid, or combination thereof, to the weight of said complex, to be in the range from about 0.5:1 to about 20:1.

A yet further embodiment the present invention relates a method for the preparation of a drug delivery system of the inventive kind comprising at least one other pharmaceutically active substance, in which the size of said other pharmaceutically active substance and the particles of said complex is controlled to have an effective average particle size of less than about 100 nm by adjusting the weight-to-weight ratio of said sodium salt of the methyl ester of N-all-trans-retinoyl cysteic acid, sodium salt of the methyl ester of N-13-cis-retinoyl cysteic acid, or combination thereof, to the combined weight of said other pharmaceutically active substance and said complex, to be in the range from about 0.5:1 to about 20:1.

Another embodiment of the invention relates to a method for the preparation of a drug delivery system of the inventive kind, in which said at least one pharmaceutically active substance is treated with a first aqueous solution of a sodium salt of the methyl ester of N-all-trans-retinoyl cysteic acid, a sodium salt of methyl ester of N-13-cis-retinoyl cysteic acid, or a combination thereof to form particles of said complex; and the formed particles of said complex are further treated in a second aqueous solution of a sodium salt of the methyl ester of N-all-trans-retinoyl cysteic acid, a sodium salt of methyl ester of N-13-cis-retinoyl cysteic acid, or a combination thereof, until said particles of said complex are dissolved in said second aqueous solution. In one aspect of this embodiment said first aqueous solution and said second aqueous solution is one and the same aqueous solution, in which aqueous solution the total amount of sodium salt of the methyl ester of N-all-trans-retinoyl cysteic acid, a sodium salt of methyl ester of N-13-cis-retinoyl cysteic acid, or a combination thereof, is sufficient to form particles of said complex; and dissolve said complex.

Another embodiment of the invention relates to a method for the preparation of a drug delivery system of the inventive kind comprising at least one other pharmaceutically active substance, in which said other pharmaceutically active substance is treated with a first aqueous solution of a sodium salt of the methyl ester of N-all-trans-retinoyl cysteic acid, a sodium salt of methyl ester of N-13-cis-retinoyl cysteic acid, or a combination thereof, until said other pharmaceutically active substance is dissolved in said first aqueous solution; said at least one pharmaceutically active substance is treated with a second aqueous solution of a sodium salt of the methyl ester of N-all-trans-retinoyl cysteic acid, a sodium salt of methyl ester of N-13-cis-retinoyl cysteic acid, or a combination thereof to form particles of said complex; and the formed particles of said complex are treated in said second aqueous solution with sodium salt of the methyl ester of N-all-trans-retinoyl cysteic acid, a sodium salt of methyl ester of N-13-cis-retinoyl cysteic acid, or a combination thereof, until said particles of said complex are dissolved in said second aqueous solution. In one aspect of this embodiment said first aqueous solution and said second aqueous solution is one and the same aqueous solution, in which aqueous solution the total amount of sodium salt of the methyl ester of N-all-trans-retinoyl cysteic acid, a sodium salt of methyl ester of N-13-cis-retinoyl cysteic acid, or a combination thereof, is sufficient to dissolve said other pharmaceutically active substance; form particles of said complex; and dissolve said complex.

Another embodiment of the present invention relates to drug delivery system obtainable by any of said inventive methods. A further embodiment of the present invention relates to a pharmaceutical composition comprising a pharmaceutically acceptable carrier and such a drug delivery system; in aspect of this embodiment the pharmaceutical composition is in the form of an aqueous solution, a gel, a cream, an ointment, a tablet, a capsule, or a softgel.

Another embodiment of the present invention relates to the use of a drug delivery system of the inventive kind for the preparation of a medicament for the treatment of cancer.

A further embodiment of the present invention relates to a method for the treatment of cancer, in which the inventive pharmaceutical composition is administered in a therapeutically effective amount to a patient in need of such treatment.

A further embodiment of the present invention relates the use of the inventive pharmaceutical composition for the preparation of a medicament for the treatment of cancer.

A further embodiment of the present invention relates to a method for the treatment of cancer, in which the inventive drug delivery system is administered in a therapeutically effective amount to a patient in need of such treatment.

The invention will be illustrated in closer detail in the following non-limiting examples.

EXAMPLES

Materials and Methods

The formulations used were either freshly prepared or obtained by reconstitution of freeze dried pharmaceutically active substances with a sodium salt of the methyl ester of N-all-trans-retinoyl cysteic acid, a sodium salt of the methyl ester of N-13-cis-retinoyl cysteic acid, or a combination thereof, by a specified solution for reconstitution.

Doxorubicin was purchased from Mercian Corporation, Japan. Paclitaxel was purchased from Sigma-Aldrich Sweden AB. Docetaxel was purchased from ScinoPharm Taiwan, Ltd. Mitoxantrone and Topotecan were purchased from Chemtronica KB, Sweden. Adriamycin was purchased from pharmacy stores and reconstituted according to manufacturers prescribing information.

The particle size of the formulations was measured by dynamic light scattering method with the use of a red laser (633 nm, Nano-ZS, Malvern Instruments Ltd). Average values of three independent measurements were calculated for plotting of particle size. Y-error bars are composed by +/− standard deviation of the measurements.

For evaluation of cytotoxicity in vitro cells of different human tumour cell lines were purchased from American Type Culture Collection (Rockville, Md., USA): Human Breast Adenocarcinoma Cell Line MDA-MB-231 (ATCC-HTB-26, Lot 3576799), Human Ovary Adenocarcinoma Cell Line SKOV-3 (ATCC-HTB-77, Lot 3038337) and Human Lung Non-Small Cancer Cell Line A549 (ATCC-CCL-185, Lot 3244171). MDA-MB-231 cells were propagated in MEM culture medium with 2 mM L-glutamine, 10% fetal bovine serum (FBS) and antibiotics. SKOV-3 cells were cultured in McCoy's 5A culture medium, supplemented with 1.5 mM L-glutamine, 10% FBS and antibiotics. All media and supplements were purchased from Sigma-Aldrich Co. (St. Louis, Mi., USA). Cell propagation of all lines was carried out in BD Falcon™ 25 or 75 $cm^2$ cultivation flasks (Becton Dickinson Labware). A549 cells were cultured in Ham's F-12 culture medium with 1 mM L-glutamine, 10% FBS and antibiotics. Cell propagation of all lines was carried out in BD Falcon™ 25 or 75 $cm^2$ cultivation flasks.

Drug cytotoxicity testing was carried out using BD Falcon™ 96-well cultivation plates for adherent cells (Becton Dickinson Labware). These plates were seeded by cells at $8×10^3$ cells/well for MDA-MB-231, at $10×10^3$ cells/well for SKOV-3 or at $6×10^3$ cells/well for A549 in a volume of 200 μl/well. Both flasks and cultivation plates were incubated for cell growth at 37° C. in a humidified atmosphere of 95% air and 5% $CO_2$.

The cell cultures in the cultivation plates were allowed to adhere for 24 hour of incubation. On day 1 after cell seeding 4 μL solutions of the formulations to be tested with different concentrations in appropriate solvents were added to wells with cultures (dose—response experiments). In the control cultures 4 μL of the solvents were added as solvent control. The cells were incubated within 2-4 consecutive days. At the end of the incubation period adherent cells were detached by trypsinization and the number of viable cells was counted using trypan blue exclusion test and a hemocytometer. All experiment were performed at least tree times and data were derived from an average of three determinations each in four replicates. The results were expressed as mean cell number±SE and the differences between control and test series evaluated by means of Student's t-test. The drug cytotoxicity was evaluated based on the extent of cell growth inhibition. The cell growth inhibition by the tested drugs was calculated as follows:

$$\text{Cell growth inhibition \%} = \frac{\text{Control} - \text{Test Series}}{\text{Control}} \times 100$$

In control series 4 μL of different solvents used for drug testing were added to cultures as negative solvent controls. The differences between these control series were insignificant; therefore an average of negative controls was applied for calculations.

Aqueous solutions of ADRIAMYCIN® (doxorubicin hydrochloride) and methanol solutions of docetaxel were used as positive controls. The differences in growth inhibition by these drugs in different solvents were insignificant; therefore an average inhibition of positive controls was applied for calculations.

The mean $IC_{50} \pm SE$ was calculated on the basis of at least three separate experiments.

Enhancement factors (EF) were calculated by dividing $IC_{50}$ of the control comparison drug with $IC_{50}$ of the inventive formulation.

Example 1

Formation of a Water Insoluble Salt of Doxorubicin and Methyl Ester of N-all-trans-retinoyl Cysteic Acid An aqueous solutions of sodium salt of methyl ester of N-all-trans-retinoyl cysteic acid (2 ml, 5 mg/mL) and doxorubicin hydrochloride (6 ml, 2 mg/ml) was prepared by mixing in a 10 ml test tube. During the mixing a fine precipitation emerged. The precipitate was separated by centrifugation of the test tube at 3000 rpm for 10 min. The supernatant was removed and the precipitate was shaken with 10 ml water followed by a new centrifugation. After three additional washing procedures as described above the supernatant was filtered through a 0.2 μm filter in order to remove possible large aggregates of the product. The solubility of the doxorubicin complex was measured by UV method at wavelength 350 nm and found to be 0.0002 mg/ml.

Example 2

Formulation of Doxorubicin, Paclitaxel and Sodium Salt of Methyl Ester of N-13-cis-retinoyl Cysteic Acid in a w/w/w Ratio 1:2.5:7

A methanol solution of paclitaxel (200 ml, 1.2 mg/ml) and sodium salt of methyl ester of N-13-cis-retinoyl cysteic acid (134.4 ml, 5 mg/ml) was prepared by mixing in a 1000 ml round-bottom flask and the solution obtained was evaporated in vacuo. The residue was dissolved in water (120 ml) and an aqueous solution of doxorubicin hydrochloride (48 ml, 2 mg/mL) was added drop-wise to the solution obtained under stirring. The combined solution was stirred for additional 30 min, filtered through a 0.2 μm filter and freeze dried.

Example 3

Formulation of Doxorubicin, Docetaxel and Sodium Salt of Methyl Ester of N-all-trans-retinoyl Cysteic Acid in a w/w/w Ratio 1:1:4

A methanol solution of docetaxel (100 ml, 1 mg/ml) and sodium salt of methyl ester of N-all-trans-retinoyl cysteic acid (80 ml, 5 mg/ml) was prepared by mixing in a 1000 ml round-bottom flask and the obtained solution was evaporated in vacuo. The residue was dissolved in water (100 ml) and an aqueous solution of doxorubicin hydrochloride (50 ml, 2 mg/mL) was added drop-wise to the obtained solution under stirring. The combined solution was stirred for additional 30 min, filtered through a 0.2 μm filter and freeze dried.

Example 4

Formulation of Mitoxantrone, Topotecan, Paclitaxel And Sodium Salt of Methyl Ester of N-all-trans-retinoyl Cysteic Acid in a w/w/w Ratio 2:1:20:40

A methanol solution of paclitaxel (200 ml, 1.2 mg/ml) and sodium salt of methyl ester of N-all-trans-retinoyl cysteic acid (96 ml, 5 mg/ml) was prepared by mixing in a 1000 ml round-bottom flask and the obtained solution was evaporated in vacuo. The residue was dissolved in water (120 ml) and an aqueous solution of mitoxantrone dihydrochloride (12 ml, 2 mg/mL) and an aqueous solution of topotecan hydrochloride (6 ml, 2 mg/ml) were added drop-wise to the obtained solution under stirring. The combined solution was stirred for additional 30 min, filtered through a 0.2 μm filter and freeze dried.

Example 5

Investigation of the Dependence of Particle Size on the Concentration of Doxorubicin in Formulation Formed by Doxorubicin, Docetaxel, Sodium Salt of Methyl Ester of N-all-trans-retinoyl Cysteic Acid and Sodium Salt of Methyl Ester of N-13-cis-retinoyl Cysteic Acid (w/w/w 1:1:1.65:1.65)

Solutions were prepared by reconstitution of freeze dried samples of mixtures of doxorubicin, docetaxel, sodium salt of methyl ester of N-all-trans-retinoyl cysteic acid and sodium salt of methyl ester of N-13-cis-retinoyl cysteic acid (w/w/w 1:1:1.65:1.65) in aqueous solution containing NaCl (5.9 mg/mL), KCl (0.3 mg/mL), $CaCl_2$ (0.295 mg/mL), $MgCl_2$ hexahydrate (0.2 mg/mL), sodium acetate (4.1 mg/Ml).

TABLE 1

| Concentration of doxorubicin, mg/ml | Average particle size, nm | St. dev. |
|---|---|---|
| 0.06 | 27.3 | 0.9 |
| 0.125 | 28.7 | 1.2 |
| 0.25 | 29.3 | 1.9 |

TABLE 1-continued

| Concentration of doxorubicin, mg/ml | Average particle size, nm | St. dev. |
|---|---|---|
| 0.5 | 34.7 | 2.1 |
| 1.0 | 48.3 | 3.1 |

As shown in Table 1 and FIG. 1 lower concentrations of doxorubicin leads to smaller particle size in concentration range 0.25-1 mg/ml. Further dilution does not significantly influence the particle size.

Example 6

Investigation of Synergism of the Action of Doxorubicin and Docetaxel in Cultures of Human Ovary Adenocarcinoma SKOV-3 Cell Line Freeze dried formulations of doxorubicin/docetaxel/methyl ester of N-all-trans-retinoyl cysteic acid/methyl ester of N-13-cis-retinoyl cysteic acid containing equimolar amounts of doxorubicin and docetaxel (w/w/w/w 1:1.4:2:2) was used. EF was calculated versus ADRIAMYCIN®. $IC_{50}$ for the docetaxel-doxorubicin mixtures is based on the sum of amounts of cytostatica. The results are set forth in Table 2 below.

TABLE 2

| Formulation | Solvent | Particle size, nm | $IC_{50}$ day 3 | EF day 3 | $IC_{50}$ day 4 | EF day 4 |
|---|---|---|---|---|---|---|
| ADRIAMYCIN ® (doxorubicin) | 9 mg/ml NaCl | — | $(8.5 \pm 0.27) \times 10^{-8}$ | — | $(4.8 \pm 0.16) \times 10^{-8}$ | — |
| Docetaxel | Methanol | — | $(9.07 \pm 0.38) \times 10^{-8}$ | — | $(2.85 \pm 0.26) \times 10^{-8}$ | — |
| Consecutive additions of ADRIAMYCIN ® and Docetaxel in mol ratio 1:1 | 9 mg/ml NaCl and methanol | — | $(2.0 \pm 0.11) \times 10^{-8}$ | 4.3 | $(4.7 \pm 0.32) \times 10^{-9}$ | 10.0 |
| Doxorubicin/docetaxel/ methyl ester of N-all-trans-retinoyl cysteic acid/methyl ester of N-13-cis-retinoyl cysteic acid (w/w/w/w 1:1.4:2:2) | NaCl (5.9 mg/mL), KCl (0.3 mg/mL), $CaCl_2$ (0.295 mg/mL), $MgCl_2$ hexahydrate (0.2 mg/mL), Na acetate (4.1 mg/mL) | 28 | $(4.6 \pm 0.27) \times 10^{-9}$ | 18.5 | $(1.8 \pm 0.08) \times 10^{-9}$ | 26.7 |

A strong synergetic effect of doxorubicin and docetaxel is indicated by the fact that EF for the consecutive additions of doxorubicin and docetaxel is >1. Reaction of nanoparticle formulation additionally increases the potency of the combination.

Example 7

Evaluation of Cytotoxicity of the Formulations in Cultures of Human Breast Adenocarcinoma MDA-MB-231 Cell Line Formulations containing a mixture of complexes of the methyl ester of N-all-trans-retinoyl cysteic acid and the methyl ester of N-13-cis-retinoyl cysteic acid were prepared by dissolving freeze dried powder. $IC_{50}$ were based on concentration of doxorubicin. Enhancement factors were calculated versus doxorubicin. The results are set forth in Table 3 below.

TABLE 3

| Formulation | Solvent | Particle size, nm | $IC_{50}$ day 3 | EF day 3 | $IC_{50}$ day 4 | EF day 4 |
|---|---|---|---|---|---|---|
| ADRIAMYCIN ® (doxorubicin) | 9 mg/ml NaCl | — | $(1.9 \pm 0.13) \times 10^{-7}$ | — | $(5.1 \pm 0.17) \times 10^{-8}$ | — |
| Doxorubicin/docetaxel/ methyl ester of N-all-trans-retinoyl cysteic acid/methyl ester of N-13-cis-retinoyl cysteic acid (w/w/w/w 1:1:1.65:1.65) | NaCl (5.9 mg/mL), KCl (0.3 mg/mL), $CaCl_2$ (0.295 mg/mL), $MgCl_2$ hexahydrate (0.2 mg/mL), Na acetate (4.1 mg/mL) | 34 | $(2.4 \pm 0.16) \times 10^{-8}$ | 7.9 | $(1.8 \pm 0.06) \times 10^{-9}$ | 28.3 |

TABLE 3-continued

| Formulation | Solvent | Particle size, nm | $IC_{50}$ day 3 | EF day 3 | $IC_{50}$ day 4 | EF day 4 |
|---|---|---|---|---|---|---|
| Doxorubicin/paclitaxel/ methyl ester of N-all-trans-retinoyl cysteic acid/methyl ester of N-13-cis-retinoyl cysteic acid (w/w/w/w 1:2.5:3:3) | NaCl (5.9 mg/mL), KCl (0.3 mg/mL), CaCl$_2$ (0.295 mg/mL), MgCl$_2$ hexahydrate (0.2 mg/mL), Na acetate (4.1 mg/mL) | 27 | $(1.1 \pm 0.11) \times 10^{-8}$ | 17.3 | $(1.5 \pm 0.07) \times 10^{-9}$ | 34.0 |

Example 8

Evaluation of Cytotoxicity of the Formulations in Cultures of Human Ovary Adenocarcinoma SKOV-3 Cell Line Formulations containing a mixture of complexes of the methyl ester of N-all-trans-retinoyl cysteic acid and the methyl ester of N-13-cis-retinoyl cysteic acid were prepared by dissolving freeze dried powder. $IC_{50}$ were based on concentration of doxorubicin. Enhancement factors were calculated versus doxorubicin. The results are set forth in Table 4 below.

TABLE 4

| Formulation | Solvent | Particle size, nm | $IC_{50}$ day 3 | EF day 3 | $IC_{50}$ day 4 | EF day 4 |
|---|---|---|---|---|---|---|
| ADRIAMYCIN ® (doxorubicin) | 9 mg/ml NaCl | — | $(8.5 \pm 0.27) \times 10^{-8}$ | — | $(4.8 \pm 0.16) \times 10^{-8}$ | — |
| Doxorubicin/docetaxel/ methyl ester of N-all-trans-retinoyl cysteic acid/methyl ester of N-13-cis-retinoyl cysteic acid (w/w/w/w 1:1:1.65:1.65) | NaCl (5.9 mg/mL), KCl (0.3 mg/mL), CaCl$_2$ (0.295 mg/mL), MgCl$_2$ hexahydrate (0.2 mg/mL), Na acetate (4.1 mg/mL) | 34 | $(9.3 \pm 0.49) \times 10^{-9}$ | 9.1 | $(3.0 \pm 0.15) \times 10^{-9}$ | 16.0 |
| Doxorubicin/paclitaxel/ methyl ester of N-all-trans-retinoyl cysteic acid/methyl ester of N-13-cis-retinoyl cysteic acid (w/w/w/w 1:2.5:3:3) | NaCl (5.9 mg/mL), KCl (0.3 mg/mL), CaCl$_2$ (0.295 mg/mL), MgCl$_2$ hexahydrate (0.2 mg/mL), Na acetate (4.1 mg/mL) | 27 | $(1.1 \pm 0.06) \times 10^{-8}$ | 7.7 | $(5.7 \pm 0.18) \times 10^{-9}$ | 8.4 |

Example 9

Evaluation of Cytotoxicity of the Formulations in Cultures of Human Lung Non-Small Cancer Cell Line A549

Formulations containing a mixture of complexes of the methyl ester of N-all-trans-retinoyl cysteic acid and the methyl ester of N-13-cis-retinoyl cysteic acid were prepared by dissolving freeze dried powder. $IC_{50}$ were based on concentration of doxorubicin. Enhancement factors were calculated versus doxorubicin. The results are set forth in Table 5 below.

TABLE 5

| Formulation | Solvent | Particle size, nm | $IC_{50}$ day 3 | EF day 3 | $IC_{50}$ day 4 | EF day 4 |
|---|---|---|---|---|---|---|
| ADRIAMYCIN ® (doxorubicin) | 9 mg/ml NaCl | — | $(1.2 \pm 0.09) \times 10^{-8}$ | — | $(2.7 \pm 0.21) \times 10^{-8}$ | — |
| Doxorubicin/docetaxel/ methyl ester of N-all-trans-retinoyl cysteic acid/methyl ester of N-13-cis-retinoyl cysteic acid (w/w/w/w 1:1:1.65:1.65) | NaCl (5.9 mg/mL), KCl (0.3 mg/mL), CaCl$_2$ (0.295 mg/mL), MgCl$_2$ hexahydrate (0.2 mg/mL), Na acetate (4.1 mg/mL) | 34 | $(2.7 \pm 0.12) \times 10^{-9}$ | 4.4 | $(3.5 \pm 0.22) \times 10^{-9}$ | 7.7 |

TABLE 5-continued

| Formulation | Solvent | Particle size, nm | IC$_{50}$ day 3 | EF day 3 | IC$_{50}$ day 4 | EF day 4 |
|---|---|---|---|---|---|---|
| Doxorubicin/paclitaxel/ methyl ester of N-all-trans-retinoyl cysteic acid/methyl ester of N-13-cis-retinoyl cysteic acid (w/w/w/w 1:2.5:3:3) | NaCl (5.9 mg/mL), KCl (0.3 mg/mL), CaCl$_2$ (0.295 mg/mL), MgCl$_2$ hexahydrate (0.2 mg/mL), Na acetate (4.1 mg/mL) | 27 | $(3.6 \pm 0.11) \times 10^{-9}$ | 3.3 | $(1.9 \pm 0.14) \times 10^{-9}$ | 14.2 |

Although the invention has been described with regard to certain embodiments, including the best mode presently known to the inventors, it should be understood that various changes and modifications as would be obvious to one having the ordinary skill in this art may be made without departing from the scope of the invention as set forth in the claims appended hereto.

The invention claimed is:

1. A drug delivery system for administration of at least one pharmaceutically active substance that is a cationic amphiphile by itself, which pharmaceutically active substance is present in the drug delivery system in particles of a complex between said pharmaceutically active substance and a sodium salt of the methyl ester of N-all-trans-retinoyl cysteic acid, a sodium salt of methyl ester of N-13-cis-retinoyl cysteic acid, or a combination thereof, said particles of said complex having an effective average particle size of less than about 50 nm, wherein
the particles of said complex are essentially amorphous;
the particles of said complex are entrapped in nanoparticles formed of a sodium salt of the methyl ester of N-all-trans-retinoyl cysteic acid, sodium salt of methyl ester of N-13-cis-retinoyl cysteic acid, or a combination thereof; and
the weight-to-weight ratio of said sodium salt of methyl ester of N-all-trans-retinoyl cysteic acid, sodium salt of methyl ester of N-13-cis-retinoyl cysteic acid, or combination thereof, to the weight of said complex is in the range from about 0.5:1 to about 20:1.

2. A drug delivery system according to claim 1, wherein said pharmaceutically active substance has a solubility per se in water of at least 4 mg/ml, and that said complex is a non-covalent complex having a solubility in water of below 0.1 mg/ml.

3. A drug delivery system according to claim 1, wherein the weight-to-weight ratio of said sodium salt of the methyl ester of N-all-trans-retinoyl cysteic acid, sodium salt of the methyl ester of N-13-cis-retinoyl cysteic acid, or combination thereof, to the weight of said complex is in the range from about 1:1 to about 10:1.

4. A drug delivery system according to claim 1, which comprises at least one other pharmaceutically active substance having a solubility per se in water of less than about 100 µg/ml, said other pharmaceutically active substance being in particulate form with an effective average particle size of less than about 100 nm, wherein
the particles of said other pharmaceutically active substance are essentially amorphous;
the particles of said other pharmaceutically active substance are entrapped together with the particles of said complex in said nanoparticles; and
the weight-to-weight ratio of said sodium salt of methyl ester of N-all-trans-retinoyl cysteic acid, sodium salt of methyl ester of N-13-cis-retinoyl cysteic acid, or combination thereof, to the combined weight of said other pharmaceutically active substance and said complex is in the range from about 0.5:1 to about 20:1.

5. A drug delivery system according to claim 4, wherein the weight-to-weight ratio of said sodium salt of the methyl ester of N-all-trans-retinoyl cysteic acid, sodium salt of the methyl ester of N-13-cis-retinoyl cysteic acid, or combination thereof, to the weight of said complex is in the range from about 1:1 to about 10:1.

6. A drug delivery system according to claim 4, wherein said other pharmaceutically active substance has an effective average particle size of less than about 50 nm, and/or said complex has an effective average particle size of less than about 50 nm.

7. A drug delivery system according to claim 4, wherein the weight-to-weight ratio of said sodium salt of the methyl ester of N-all-trans-retinoyl cysteic acid, sodium salt of the methyl ester of N-13-cis-retinoyl cysteic acid, or combination thereof, to the combined weight of said other pharmaceutically active substance and complex is in the range from about 1:1 to about 10:1.

8. A drug delivery system according to claim 1, wherein at least one of said pharmaceutically active substances is a cytotoxic or a cytostatic compound.

9. A drug delivery system according to claim 8, wherein said cytotoxic or cytostatic compound is a protonated form of doxorubicin, mitoxantrone, epirubicin, daunorubicin, idarubicin, topotecan, irinotecan, vinblastine, vincristine, vinorelbine, amsacrine, procarbazine, mechlorethamine, or a combination thereof.

10. A drug delivery system according to claim 4, wherein said other pharmaceutically active substance is a cytotoxic or cytostatic compound.

11. A drug delivery system according to claim 10, wherein said cytotoxic or cytostatic compound is a taxane.

12. A drug delivery system according to claim 11, wherein said taxane is chosen among paclitaxel, docetaxel, and derivatives thereof.

13. A drug delivery system according to claim 4, wherein said at least one pharmaceutically active substance and said other pharmaceutically active substance are cytotoxic or cytostatic compounds.

14. A drug delivery system according to claim 13, wherein said at least one pharmaceutically active substance is a protonated form of doxorubicin, mitoxantrone, epirubicin, daunorubicin, idarubicin, topotecan, irinotecan, vinblastine, vincristine, vinorelbine, amsacrine, procarbazine, mechlorethamine, or a combination thereof.

15. A drug delivery system according to claim 13, wherein said other pharmaceutically active substance is a taxane.

16. A drug delivery system according to claim 15, wherein said taxane is chosen among paclitaxel, docetaxel, and derivatives thereof.

17. A drug delivery system according to claim 1 for use in treatment of cancer.

18. A pharmaceutical composition comprising a pharmaceutically acceptable carrier and the drug delivery system according to claim 1.

19. A pharmaceutical composition according to claim 18 in the form of an aqueous solution, a gel, a cream, an ointment, a tablet, a capsule, or a softgel.

20. A method for the preparation of a drug delivery system according to claim 1, in which the size of said complex is controlled to have an effective average particle size of less than about 100 nm by adjusting the weight-to-weight ratio of said sodium salt of the methyl ester of N-all-trans-retinoyl cysteic acid, sodium salt of the methyl ester of N-13-cis-retinoyl cysteic acid, or combination thereof, to the weight of said complex, to be in the range from about 0.5:1 to about 20:1.

21. A method for the preparation of a drug delivery system according to claim 4, in which the size of said other pharmaceutically active substance and the particles of said complex is controlled to have an effective average particle size of less than about 100 nm by adjusting the weight-to-weight ratio of said sodium salt of the methyl ester of N-all-trans-retinoyl cysteic acid, sodium salt of the methyl ester of N-13-cis-retinoyl cysteic acid, or combination thereof, to the combined weight of said other pharmaceutically active substance and said complex, to be in the range from about 0.5:1 to about 20:1.

22. A method for the preparation of a drug delivery system according to claim 1, in which
said at least one pharmaceutically active substance is treated with a first aqueous solution of a sodium salt of the methyl ester of N-all-trans-retinoyl cysteic acid, a sodium salt of methyl ester of N-13-cis-retinoyl cysteic acid, or a combination thereof to form particles of said complex; and
the formed particles of said complex are further treated in a second aqueous solution of a sodium salt of the methyl ester of N-all-trans-retinoyl cysteic acid, a sodium salt of methyl ester of N-13-cis-retinoyl cysteic acid, or a combination thereof, until said particles of said complex are dissolved in said second aqueous solution.

23. A method according to claim 22, in which said first aqueous solution and said second aqueous solution is one and the same aqueous solution, in which aqueous solution the total amount of sodium salt of the methyl ester of N-all-trans-retinoyl cysteic acid, a sodium salt of methyl ester of N-13-cis-retinoyl cysteic acid, or a combination thereof, is sufficient to
form particles of said complex; and
dissolve said complex.

24. A method for the preparation of a drug delivery system according to claim 4, in which
said other pharmaceutically active substance is treated with a first aqueous solution of a sodium salt of the methyl ester of N-all-trans-retinoyl cysteic acid, a sodium salt of methyl ester of N-13-cis-retinoyl cysteic acid, or a combination thereof, until said other pharmaceutically active substance is dissolved in said first aqueous solution;
said at least one pharmaceutically active substance is treated with a second aqueous solution of a sodium salt of the methyl ester of N-all-trans-retinoyl cysteic acid, a sodium salt of methyl ester of N-13-cis-retinoyl cysteic acid, or a combination thereof to form particles of said complex; and
the formed particles of said complex are treated in said second aqueous solution with sodium salt of the methyl ester of N-all-trans-retinoyl cysteic acid, a sodium salt of methyl ester of N-13-cis-retinoyl cysteic acid, or a combination thereof, until said particles of said complex are dissolved in said second aqueous solution.

25. A method according to claim 24, in which said first aqueous solution and said second aqueous solution is one and the same aqueous solution, in which aqueous solution the total amount of sodium salt of the methyl ester of N-all-trans-retinoyl cysteic acid, a sodium salt of methyl ester of N-13-cis-retinoyl cysteic acid, or a combination thereof, is sufficient to
dissolve said other pharmaceutically active substance;
form particles of said complex; and
dissolve said complex.

26. A drug delivery system obtainable by the method according to claim 20.

27. A pharmaceutical composition comprising a pharmaceutically acceptable carrier and a drug delivery system according to claim 26.

28. A pharmaceutical composition according to claim 27 in the form of an aqueous solution, a gel, a cream, an ointment, a tablet, a capsule, or a softgel.

29. A method for the treatment of cancer, wherein a pharmaceutical composition according to claim 18 is administered in a therapeutically effective amount to a patient in need of such treatment.

30. A method for the treatment of cancer, wherein a drug delivery system according to claim 1 is administered in a therapeutically effective amount to a patient in need of such treatment.

* * * * *